United States Patent [19]

Fitzpatrick

[11] Patent Number: 4,755,752

[45] Date of Patent: Jul. 5, 1988

[54] FLAW IMAGING IN FERROUS AND NONFERROUS MATERIALS USING MAGNETO-OPTIC VISUALIZATION

[75] Inventor: Gerald L. Fitzpatrick, 19226 SE. 46th Pl., Isaaquah, Wash. 98027

[73] Assignee: Gerald L. Fitzpatrick, Issaquah, Wash.

[21] Appl. No.: 886,217

[22] Filed: Jul. 16, 1986

Related U.S. Application Data

[63] Continuation-in-part of Ser. No. 510,662, Jul. 5, 1983, Pat. No. 4,625,167.

[51] Int. Cl.[4] .................. G01N 27/82; G01N 21/21; G02F 1/09
[52] U.S. Cl. .................................. 324/228; 324/200; 324/213; 324/260; 350/377; 356/237
[58] Field of Search ................ 324/200, 226, 213–216, 324/228, 235, 244, 262, 96, 260; 250/225; 350/374–378; 356/237

[56] References Cited

U.S. PATENT DOCUMENTS

| | | | |
|---|---|---|---|
| 3,443,214 | 5/1969 | Meservey | 324/214 |
| 3,564,924 | 2/1971 | Desorbo | 324/244 X |
| 3,588,223 | 6/1971 | Watson | 350/151 |
| 3,594,064 | 7/1971 | Bierlein | 350/377 X |
| 3,650,601 | 3/1972 | Bierlein | 350/377 X |
| 3,893,023 | 7/1975 | Otala | 324/244 |
| 4,064,453 | 12/1977 | Haas et al. | 324/244 X |
| 4,540,284 | 9/1985 | Gavert et al. | 350/377 X |

FOREIGN PATENT DOCUMENTS

| | | | |
|---|---|---|---|
| 2304076 | 10/1976 | France . | |
| 0058461 | 4/1983 | Japan | 324/214 |
| 0697905 | 11/1979 | U.S.S.R. | 324/216 |

OTHER PUBLICATIONS

Eiwa Denki K.K., "Apparatus For Inspecting Defects Of Steel Products", Patent Abstracts of Japan, vol. 1, No. 119, 11 Oct. 1977, p. 4781E77.

Falk et al., "Optical Detection Of Magnetic Stray Fields", Optics Communications, vol. 24, No. 1, Jan. 1978 pp. 129-132.

Primary Examiner—Gerard R. Strecker
Attorney, Agent, or Firm—Blakely Sokoloff Taylor & Zafman

[57] ABSTRACT

A method for the direct visualization of surface and near surface cracks, voids, flaws, discontinuities, etc. in a material is disclosed. The detection of flaws or the like is accomplished by the visualization of the static and/or dynamic magnetic fields, either ambient or induced, associated with various flaws in a target material. A magnetic garnet epitaxial film is deposited on either side of a non-magnetic substrate. In one embodiment, a reflective coating or material is provided adjacent to the epitaxial film, and the substrate with its associated layers is placed over the target material. A magnetic field is then applied to the target material and substrate. Polarized light is transmitted onto the target material and is reflected through the epitaxial layer and back out of the substrate. The existing magnetization within the epitaxial film interacts with nearby magnetic fields associated with near surface flaws in the target material, such that the domain structure of the epitaxial film is altered. The altered domain structure induces a rotation of the plane of polarization of the incident projected light. When viewed through a polarizing material disposed on the top epitaxial layer, the rotation of the reflected light renders the magnetic field variations associated with the flaws directly visible. Accordingly, surface and near surface flaws are optically detected.

14 Claims, 4 Drawing Sheets

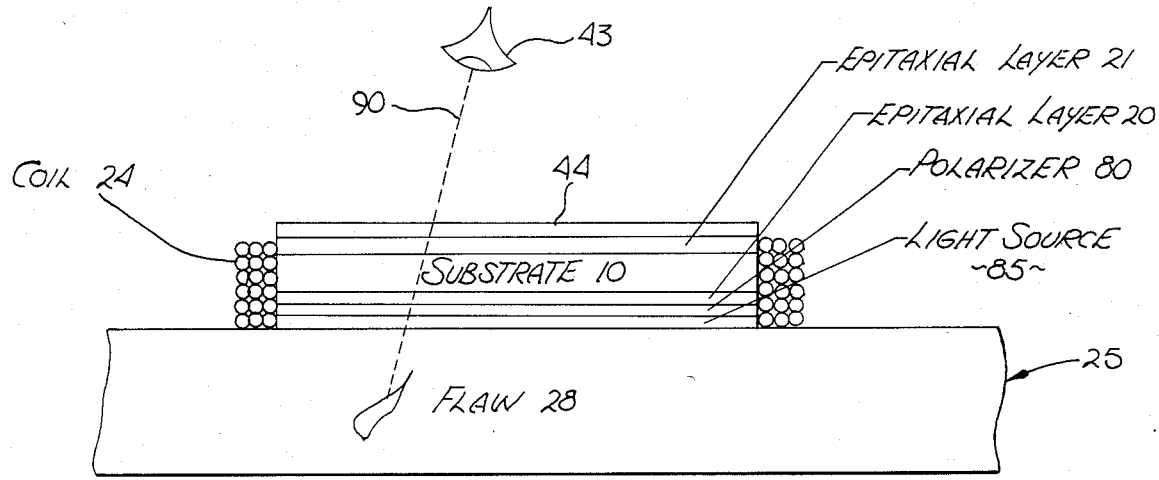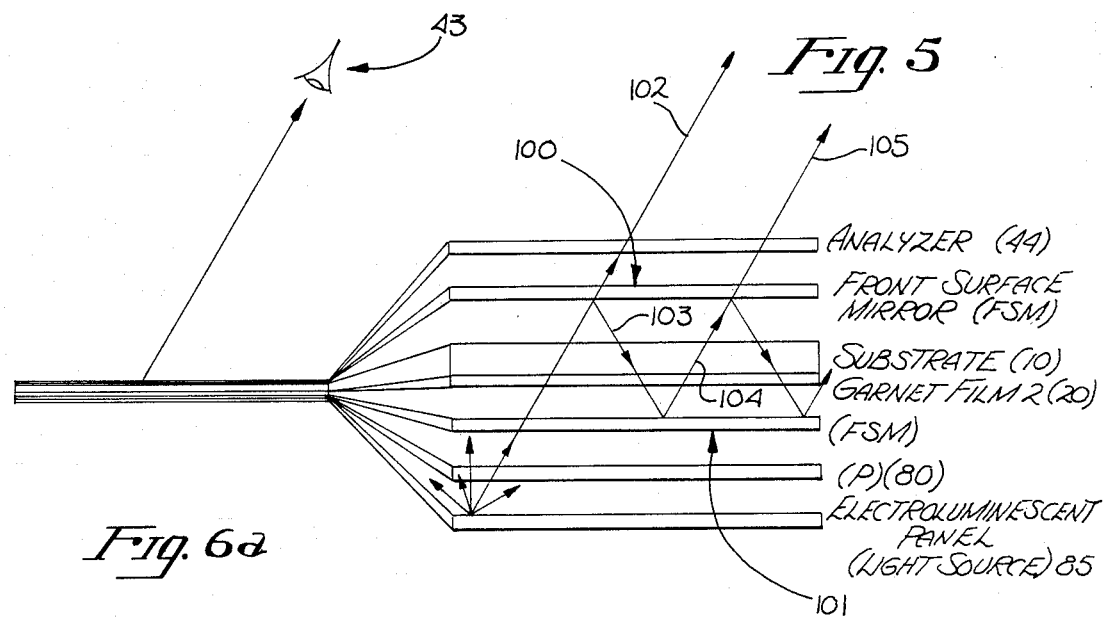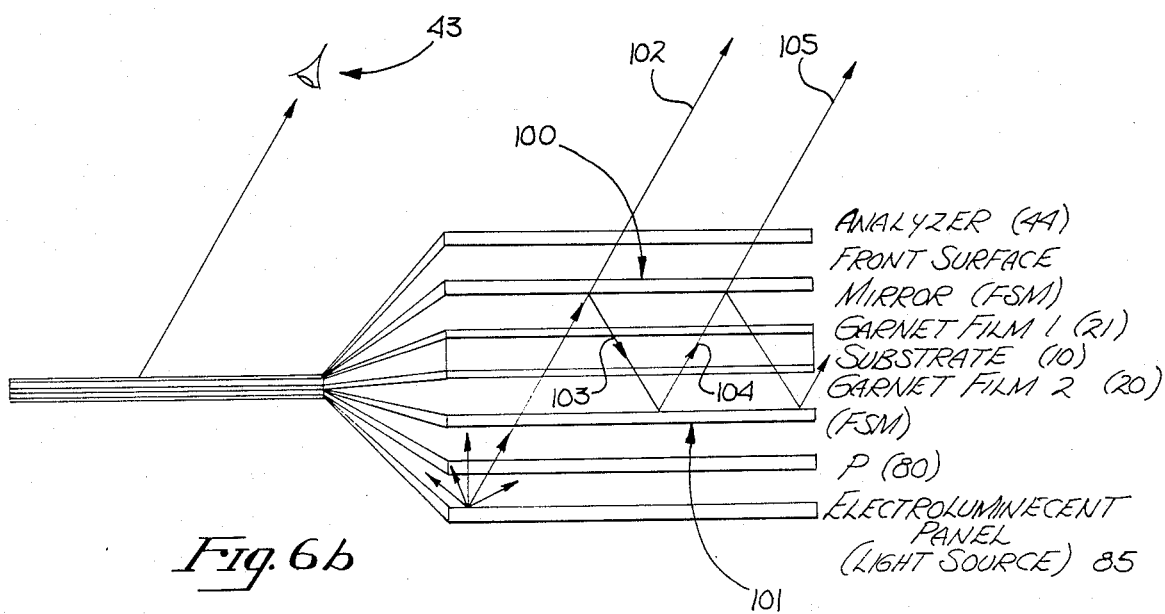

FLAW IMAGING IN FERROUS AND NONFERROUS MATERIALS USING MAGNETO-OPTIC VISUALIZATION

The present application is a continuation-in-part of U.S. patent application, Ser. No. 510,662, filed July 5, 1983, now U.S. Pat. No. 4,625,167 issued Nov. 25, 1986.

BACKGROUND OF INVENTION

1. Field of the Invention

The present invention relates to the field of detecting flaws and discontinuities in materials, and more particularly, to the detection of flaws and discontinuities in materials using magneto-optic visualization.

2. Art Background

In many scientific, engineering and manufacturing applications, near surface cracks, voids, discontinuities and flaws in ferrous or nonferrous materials must be detected in order to insure the structural integrity of a material. For example, the material integrity of components comprising many air and space vehicles is critical for their proper operation, especially with regard to high stress components such as turbine and fan blades, rocket engine systems, air frames, etc.

A number of techniques have been developed and utilized in order to detect cracks, flaws, or the like, in materials. For example, magnetic particle methods have been employed which utilize static or "low" frequency (less than 100 Hz) magnetic fields having field components parallel to the surface of ferrous alloys which are induced by currents paralleling these surfaces. The parallel surface currents in turn may be induced, either directly, by contact electrodes, or indirectly, using coils surrounding the target material and low frequency excitation. Magnetic fields paralleling the surfaces of the target material are distorted by cracks or near surface flaws and these distortions may be detected through the use of a magnetic powder deposited on the material. Various types of magnetic powders have been developed for the visualization of sub-surface flaws. Each magnetic particle in thse powders typically consists of a single magnetic domain (i.e. a region of essentially uniform magnetization). When the magnetic powder is applied dry or in a wet slurry to a target material where a crack or flaw is present, the magnetic particles tend to aggregate and form a bridge in regions of field non-uniformities which are associated with the flaw. By mixing various pigments, flourescent dyes, and the like, with the magnetic powder, the cracks or flaws are rendered visible.

Although the magnetic powder technique is widely employed, it is a dirty and time consuming method which requies the induction of large surface currents in the material under study. Magnetic particle methods are best suited for use with low frequencies and ferrous alloys. The large masses of magnetic particles required renders the magnetic powder techniques ineffective when high frequencies are used.

Another method which has been utilized in order to detect flaws or cracks in materials is the "eddy" current technique. Eddy current techniques typically utilize a time varying electro-magnetic field which is applied to the target material being examined. Non-contact coils may then be used to excite eddy currents in the target material, such that these currents tend to flow around flaws and result in field distortions which allow the flaw to be detected in a number of well known ways. For example, circuit parameters characterizing the mutual interaction between the exciting coil and the responding material may comprise the parameters of capacitance, inductance or reactance. However, eddy current techniques require a considerable amount of support equipment and most techniques do not result in a flaw image but rather produce data from which flaw information can be obtained only after appropriate analysis has been completed.

As will be described, the present invention provides a method for the direct optical visualization of surface and near surface cracks, flaws, etc. in ferrous and nonferrous materials. The present invention provides direct visualization of both the static and/or dynamic magnetic fields associated with the various flaws or other discontinuities in a target material, and overcomes the disadvantages associated with prior art material flaw imaging methods. In addition, the present invention is compatible with the requirements of eddy current methods while producing images of flaws directly, without the additional support equipment and data analysis required by most eddy current systems.

SUMMARY OF THE INVENTION

A method for the direct visualization of surface and near surface cracks, voids, flaws, discontinuities, etc. in a material is disclosed. The detection of flaws or the like is accomplished by the visualization of the static and/or dynamic magnetic fields, either ambient or induced, associated with various flaws in a target material.

A magnetic garnet epitaxial film is deposited on either side of a non-magnetic substrate. In one embodiment, a reflective coating or material is provided adjacent to the epitaxial film, and the substrate with its associated layers is placed over the target material. A magnetic field is then applied to the target material and substrate. Polarized light is transmitted onto the target material and is reflected through the epitaxial layer and back out of the substrate. The existing magnetization within the epitaxial film interacts with nearby magnetic fields associated with near surface flaws in the target material, such that the domain structure of the epitaxial film is altered. The altered domain structure induces a rotation of the plane of polarization of the incident projected light When viewed through a polarizing material disposed on the top epitaxial layer, the rotation of the reflected light renders the magnetic field variations associated with the flaws directly visible. Accordingly, surface and near surface flaws are optically detected.

BRIEF DESCRIPTION OF THE DRAWINGS

FIG. 5 illustrates the present invention with the addition of an analyzer layer on the imaging device.

FIG. 6(a) illustrates the present invention with the addition of a pair of front surface mirror layers, in conjunction with a single epitaxial layer, transmission configuration.

FIG. 6(b) illustrates the embodiment df FIG. 6(a) with the addition of a second epitaxial layer.

DETAILED DESCRIPTION OF THE INVENTION

A method for magneto-optically visualizing flaws, inclusions, voids, discontinuities, etc. (hereinafter collectively referred to as "flaws") in ferrous and nonferrous materials is disclosed. In the following description for purposes of explanation, numerous details are set forth such as specific garnet materials, substrates, optical configurations, magnetic fields, currents, frequencies, etc. in order to provide a thorough understanding of the present invention. However, it will be apparent to one skilled in the art that the invention may be practiced without these specific details. In other instances, well known optical components, structures and electrical processing means have not been described in detail in order not to obscure the present invention unnecessarily.

Figure 1:
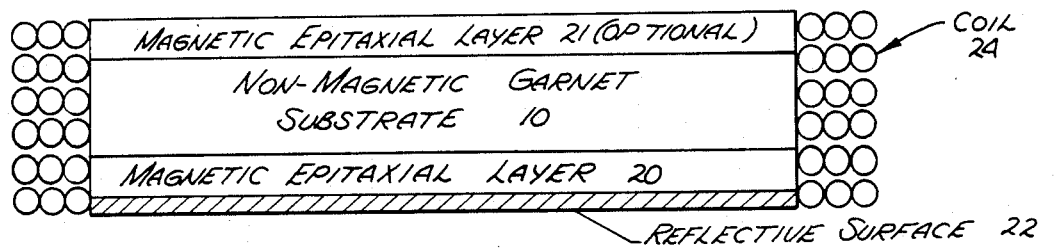
FIG. 1 illustrates an epitaxial garnet film and reflective coating disposed on a non-magnetic substrate.

Referring now to FIG. 1, the presently preferred embodiment of the invention utilizes a non-magnetic garnet substrate 10 on which magnetic garnet epitaxial layer 20 and an optional layer 21 is disposed. As shown, a reflective surface 22 is provided using well known deposition techniques or materials on the epitaxial layer 20, such that incident light passing through the substrate 10 and layers 20 and 21 is reflected back through layer 20, substrate 10 and layer 21, and flaws thereby imaged in a manner which will be discussed more fully below. It will be noted that the reflective surface 22 may comprise a front surface mirror or "Scotchlite" type coating (which is a retroreflective coating), as well as other numerous deposited reflective coatings. As shown in FIG. 1, an electrical coil 24 is disposed around substrate 10 with its associated layers. As will be discussed, coil 24 is provided with an electric potential in order to induce a current I in the coil which produces a magnetic field through both substrate 10 and magnetic layers 20 and 21, as well as a target material which is to be tested for flaws or other discontinuities. For purposes of this Specification, the term "epitaxial layer" or "epitaxial garnet layer" is understood to mean any one of a variety of suitable magneto-optically active film types having magneto-optic activity as required by the present invention for any particular application.

Figure 2A:
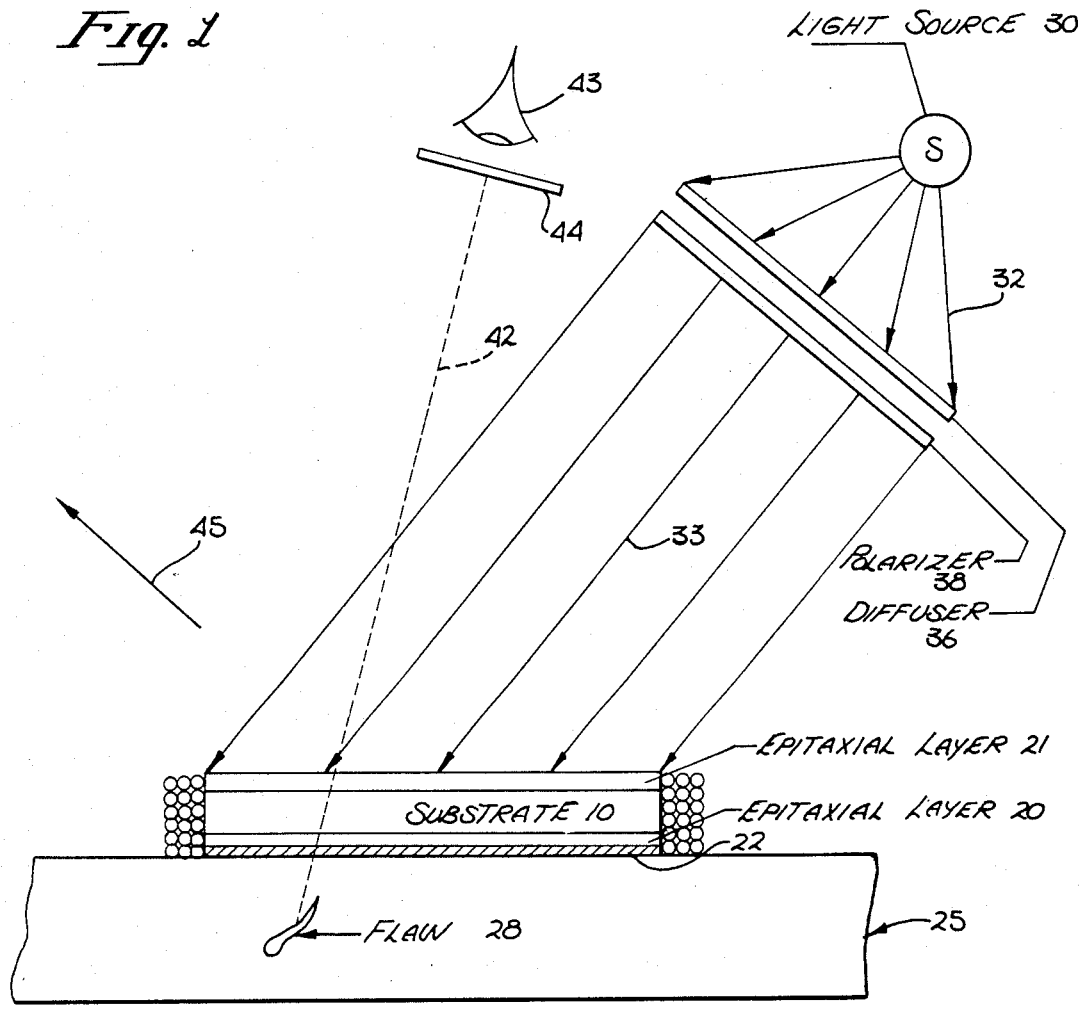
FIG. 2(a) illustrates one embodiment of the present invention utilizing a reflection geometry to optically detect flaws within a test material.

With reference now to FIG. 2(a), one embodiment of the present invention is disclosed which utilizes a reflection geometry. A target material 25 is provided which may include an unknown flaw 28 within the structure of the material 25. Substrate 10 with its magnetic epitaxial layers 20 and 21 is disposed over a portion of the target material 25 to be examined. A magnetic field is applied to the test material 25 and substrate 10 with its applied layers 20, 21 and 22 by passing a current through coil 24 or, alternatively, by attaching electrodes to the material. A light source 30 which may comprise, for example, an incandescent bulb, single wave-length laser fluorescent lamp, or the like, is provided in order to generate incident light beams 32. A diffuser 36 is provided to diffuse light rays 32 generated by light source 30. Similarly, a polarizer 38 is disposed adjacent to, and in optical alignment with, the diffuser 36 such that light generated by light source 30 is linearly polarized after passing through diffuser 36. As shown in FIG. 2(a), the now polarized light 33 is projected onto the substrate 10 with associated layers disposed above the target material 25, and, as will be discussed more fully below, flaws 28 are rendered directly visible by observing the reflected radiation 42 reflected off of reflective surface 22 and passing through a second polarizer 44. As shown, unwanted surface reflections 45 are reflected off of layer 21 and away from the second polarizer 44.

When the polarized light 33 is incident on the magnetic garnet epitaxial layer 20, the plane of polarization of the incident light will be rotated by an angle which may be described by the following relationship:

$$\theta \propto \theta_f \overline{K} \cdot \overline{M}$$

Where $\theta_f$ is the specific faraday rotation of the layer 20, $\overline{K}$ is the wavevector of the incident light, and the $\overline{M}$ is the local magnetization of the epitaxial layer 20 at the point where the incident light passes through the layer. The sign of the scalar product $\overline{K} \cdot \overline{M}$ determines the sense of the rotation. It will be noted that in the case of a solid, the Faraday rotation does not depend on the sign of the wavevector $\overline{K}$, but only on the angle between $\overline{K}$ and $\overline{M}$. Thus, the effect of rotation is doubled by the reflective surface 22 disposed between the upper surface of the target material 25 and the magnetic garnet epitaxial layer 20. The reflective surface 22 ensures that the incident light 33 will pass back through the epitaxial layer 20 and thereby double the effective rotation of the plane of polarization. It will be appreciated that although not required, the presently preferred embodiment includes second epitaxial layer 21 disposed above substrate 10. This second layer 21 is generally separated from lower layer 20 by approximately 0.02 inches (the thickness of substrate 10), and has been found to increase the sensitivity of the present invention and improve contrast. However, for purposes of clarity, the analysis of the operation of the present invention disclosed hereinbelow will assume layer 21 is not present.

The difference in the rotation of the plane of polarization of the incident linearly polarized light 33 and the reflected light 42 which passes through the epitaxial layer 20 permits the direct visualization of flaws within material 25. In addition, it has been found that the present invention also permits the visualization of the existing state of magnetization in materials 25 due to prior magnetic history or present conditions such as electromagnetic fields, stress fields, or temperature gradients. Ordinarily, in the absence of an applied magnetic field, magnetic domains (regions of uniform magnetization in the epitaxial layer 20) are relatively small. In many epitaxial magnetic garnet films, especially those used in magnetic bubble memories or the like, domains typically measure several microns across. In other epitaxial films, small applied fields (of, for example, 100 Gauss or less) can cause the magnetic domains to coalesce into large domains several centimeters across in epitaxial layers having only slightly larger dimensions.

Figure 3:
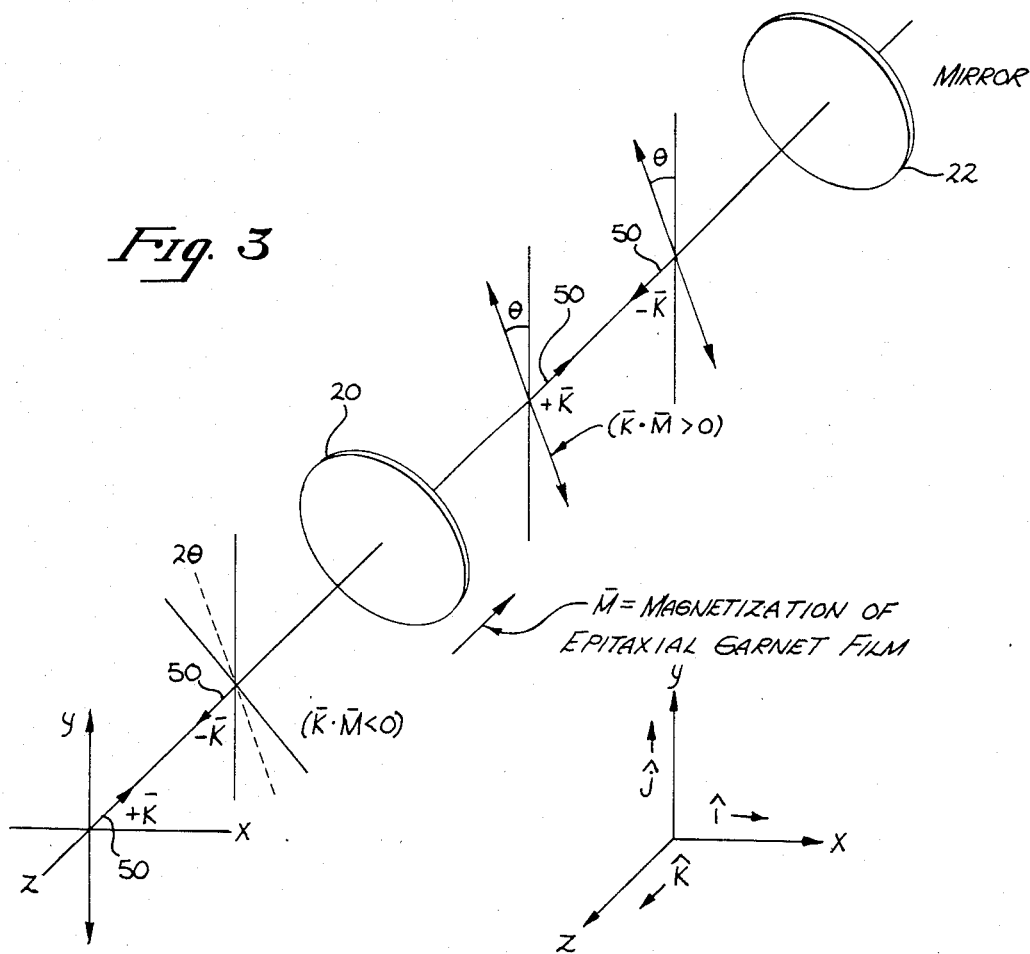
FIG. 3 illustrates the Faraday effect of a magneto-optically active garnet film on the plane of polarization of an incident light wave.

Referring now to FIG. 3, the effect of a magnetic garnet epitaxial layer 20 on the plane of polarization of incident light 33 is illustrated. A light wave 50 which is one representative ray of incident light 33 has a wave vector $+\overline{K}$ along the negative Z axis which is linearly polarized along the Y axis. As light wave 50 passes through epitaxial layer 20 travelling toward surface 22, the polarization of light wave 50 is rotated counterclockwise by an angle $\theta$. As light wave 50 impinges on reflective surface 22, the wave vector is reversed and light wave 50 again passes through the epitaxial layer 20. Thus, a doubled Faraday rotation of the polarization of wave 50 occurs such that the plane of polarization of the light wave 50 is now $2\theta$ with reference to the Y axis or original polarization direction.

Figure 4A:
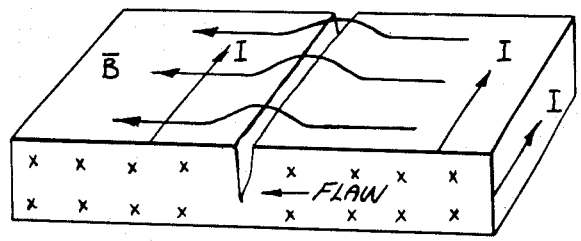
FIG. 4(a) illustrates magnetic fields induced by currents which effectively "jump" a flaw or other discontinuity in a test material.
Figure 4B:
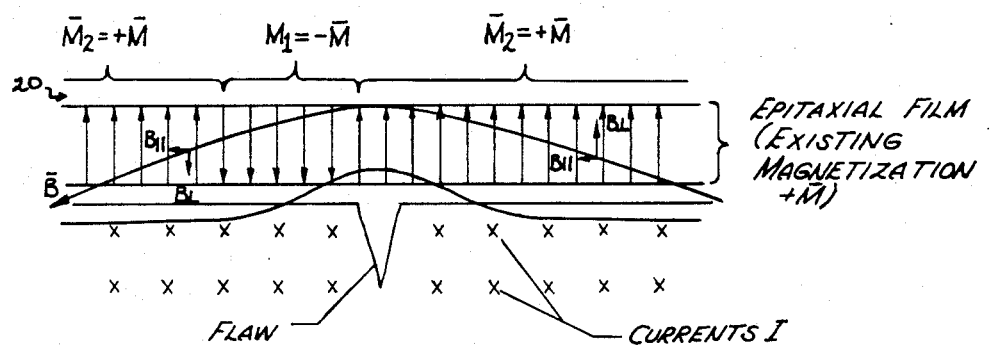
FIG. 4(b) illustrates the domain structure of the epitaxial layer in the pressence of a magnetic field.
Figure 4C:
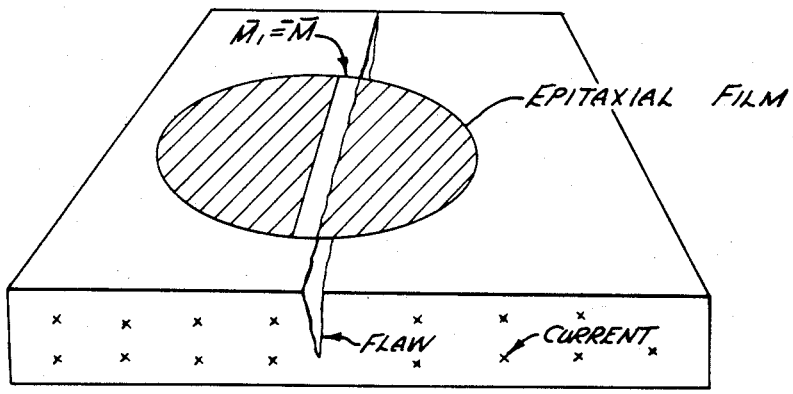
FIG. 4(c) illustrates an image, magneto-optically produced, of a flaw within a test material using the teachings of the present invention.

Referring now to FIGS. 4(a)-(c), it will be appreciated that the magnetic fields associated with a flaw are capable of switching the direction of existing magnetization at some point in the epitaxial layer 20 from $+\overline{M}$ to $-\overline{M}$. As shown in FIG. 4(a), a small flaw 28 has an associated magnetic field ("B field") distortion which will switch the magnetization of epitaxial layer 20 in regions parallel to the flaw [see FIG. 4(b)]. The plane of polarization of the light which passes through the region with magnetization $\overline{M}_1 = -\overline{M}$ is rotated by an angle $$\theta_1 \propto \overline{K}_1 \cdot \overline{M}_1 > 0$$

but the plane of polarization of the light that passes through the adjacent region with magnetization $\overline{M}_1 = +\overline{M}$ is rotated by an angle $$\theta_2 \propto \overline{K}_1 \cdot \overline{M}_2 < (|\theta_1| \simeq |\theta_2| \simeq \theta)$$

Thus, the total angle between the planes of polarization of the two light waves initially is zero, whereas after passing through the two adjacent regions having opposite magnetization it is:

$$2\theta \simeq |\theta_1| + |\theta_2|$$

As indicated in FIG. 3, the effect of reflective surface 22 is to double the angle of rotation of polarization, resulting in an angle of $4\theta$ between the planes of polarization of the two light waves upon passage back through the epitaxial layer 20. The light 42 which is returned to the viewer 43 is passed through a second polarizer 44 (referred to as an "analyzer"), and the flaw or other subsurface defect is thereby detected. In practice, this is accomplished by setting the analyzer 44 to block one and pass the other of two light waves, the planes of polarization of which are separated by an angle of 4 when two epitaxial layers 20 and 21 are used. Thus, two adjacent regions having reversed magnetization $\overline{M}_1$ and $\overline{M}_2$ in each of the two epitaxial layers 20 and 21 are seen as being dark (light) or light (dark) respectively, depending on the setting of the analyzer 44. In other words, the region of "reversed" magnetization adjacent to the flaw boundary is rendered visible as illustrated in FIG. 4(c).

Thus, the present invention images perturbations of the state of existing magnetization in a particular region of the epitaxial layer 20, by either changing the magnitude and direction of the existing magnetization, or reversing (switching) the magnetization in the region of layer 20 above the flaw in material 25 altogether. These purturbations are then visually "imaged" by the returned polarized light 42 through the use of polarizing analyzer 44. The addition of optional layer 21 does not alter the operation of the present invention but rather further doubles the rotation of the plan of polarization of the incident light 33.

Figure 2B:
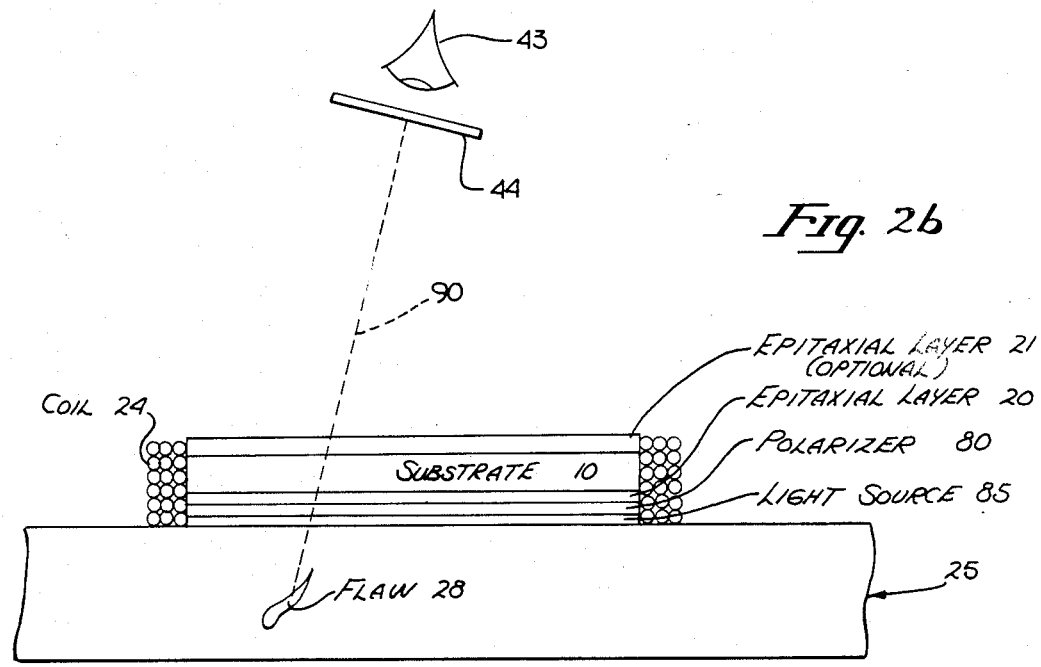
FIG. 2(b) illustrates another embodiment of the present invention utilizing a transmission geometry in order to optically detect flaws within a test material.

Referring briefly to FIG. 2(b), an alternate embodiment of the present invention is disclosed wherein a transmission geometry is utilized. As in the embodiment illustration in FIG. 2(a), a non-magnetic substrate 10 is provided on which magnetic garnet epitaxial layer 20 and optional epitaxial layer 21 are disposed. A linear polarizer 80 is sandwiched between the epitaxial layer 20 and diffuse light source 85, such as an electroluminescent panel coupled to a voltage source. As shown, the substrate 10, magnetic epitaxial layers 20 and 21, polarizer 80, and the diffuse light source 85 are surrounded by coil 24 and form an assembly which is placed in contact with material 25 to be tested having a flaw 28. The diffuse light source 85 generates light which passes upwardly through polarizing layer 80, layer 20, substrate 10, and through epitaxial layer 21. By viewing the light 90 passing through epitaxial layer 20, or through the epitaxial layers 20 and 21, through polarizer 44, magnetic field reversals and other magnetic field perturbations caused by flaw 28 in epitaxial layer 20 may be directly viewed. Thus, the theory of operation of the embodiment disclosed in FIG. 2(b) is substantially the same as that described with reference to FIG. 2(a). Accordingly, just as in the case of FIG. 2(a), flaws are rendered visible as a result of the rotation of the plane of polarization of incident light passing through layer 20 and optional layer 21.

The foregoing disclosure related to the present invention assumed frequencies being substantially zero. It will be apparent to one skilled in the art, that if the magnetic fields are reversed, due to current reversals or the like (i.e. AC signals), these fields are capable of switching the magnetization of the epitaxial layer 20 from $+\overline{M}$ to $-\overline{M}$. In such an event, the pattern of light and dark as seen through the polarizing analyzer 44 is in synchrony with these current reversals. If an alternating field is present, as is the case of the eddy current methods known in the prior art, it will be apparent that the image viewed through the analyzer 44 would tend to average to some uniform value and therefore "wash out" the flaw image. There are a number of methods which may be used in order to preserve the flaw image in the case of current reversals. One solution is to amplitude modulate the illumination of the epitaxial layer 20 at the same frequency and in some fixed phase relation with the current reversals. Similarly, it is possible to amplitude modulate the induced currents in the test material 25. Moreover, for very low frequency applications it is possible to "chop" the incident light wave 33 of FIG. 2(a) in synchrony with the applied magnetic fields. For higher frequency applications the incident light 33 could be amplitude modulated with various devices.

By amplitude modulating the incident light 33 in this or some other manner, dark areas of a scene would always be viewed by a detector, or the eye, through analyzer 44 as dark, and light areas of the scene would always appear light. Thus, the flaw 28 could be directly viewed even in the situation where the fields vary in time (e.g. the eddy current case). By adjusting the frequency of the electromagnetic field which excites the eddy currents, one can control the skin depth (the depth of penetration of the exitation wave), and therefore obtain information relative to the depth of the flaws detected by the present invention's method.

Pulsed direct currents or amplitude modulated electromagnetic fields, which excite essentially pulsed direct currents in the test material 25, may also be employed in order to utilize the present invention where the fields are varying in time. Accordingly, when viewing a scene through the analyzer 44, the magnetization directions in the epitaxial layer under conditions of constant light intensity would tend to maintain their direction and thus the image of flaws within the material 25 would be rendered visible and not washed out as in the case of time varying currents and fields.

FIG. 5 illustrates an embodiment of the present invention utilizing a transmission geometry scheme as described in conjunction with FIG. 2(b). However, in this embodiment, an analyzer layer 44 is disposed on the surface of upper epitaxial layer 21. The analyzer layer 44 polarizes the light transmitted through the polarizer 80, the lower epitaxial layer 20, substrate 10 and upper epitaxial layer 21, enabling magnetic field reversals and other magnetic field perturbations caused by flaws, such as flaw 28, to be directly viewed. By disposing the analyzer layer 44 directly on epitaxial layer 21, a more compact viewing device may be realized. In addition, there are no problems with alignment between the flaw imaging device and the analyzer 44, such as may arise when the embodiment illustrated in FIG. 2(b) is utilized.

As with the embodiment illustrated in FIG. 2(b), the present embodiment can be employed using only a single epitaxial layer 20 with upper epitaxial layer 21 eliminated. In this embodiment, analyzer layer 44 is disposed on the upper surface of substrate 10. Light from light source 85 is transmitted through polarizer 80, epitaxial layer 20 and substrate 10 through analyzer 44 into the viewer 43. The use of a single epitaxial layer still allows magnetic field reversals and other perturbations to be observed, thus identifying flaw locations.

It may be desired to utilize the imaging device of the present invention under ambient light conditions (e.g. bright room lights). Such an embodiment is illustrated in FIGS. 6(a) and 6(b). This alternate embodiment utilizes a pair of front surface mirrors (FSM), i.e. partially reflecting mirrors, on either side of the magnetic material.

As shown in FIG. 6(a), FSM 100 is disposed on the upper surface of substrate 10 and FSM 101 is disposed between epitaxial layer 20 and polarizing layer 80. An electro-luminescent panel 85 is disposed between the polarizer 80 and the target material. An analyzer 44 may be disposed on the upper surface of FSM layer 100 or disposed separately from the imaging device.

In this embodiment, the mirrors are 50% reflective, meaning that 50% of the light striking the mirror is transmitted and 50% is reflected. However, partially reflecting mirrors which transmit different amounts of light striking the surface of the mirror may be utilized as well.

In operation, light from the light source 85 strikes the low surface of FSM 101. Fifty percent (50%) of this light is transmitted through FSM 101 through the magnetic material [epitaxial layer 20 and substrate 10 in FIG. 6(a)] and on to FSM 100. Fifty percent (50%) of this light originally striking FSM 100 is transmitted through the analyzer 44 and to the viewer. This amount is represented by ray 102. Fifty percent (50%) of this original light striking FSM 100 is reflected back through the magnetic material and is represented by ray 103. This light strikes FSM 101 and 50% of it (ray 104) is reflected back through the magnetic material on to FSM 100. Again, 50% of this light (ray 105) is transmitted through FSM 100 and analyzer 44 to the viewer.

The configuration shown in FIG. 6(a) allows the present invention to be used in spite of ambient room light. Fifty percent (50%) of the ambient room light is reflected by FSM 100. Thus, the ambient room light does not interfere with the imaging of the flaw in the target material. In addition, because light is internally reflected by the FSM layers, the effect is to more than double the angle of rotation of polarization. (See FIG. 3.) As shown in FIG. 6(b), a second garnet film layer 21 may be disposed between the substrate 10 and FSM 100.

The present invention may be utilized for imaging flaws in both ferrous and nonferrous materials. Due to the large magnetic permeability of ferrous materials (e.g. iron or steel) the magnetic field inside ferrous materials is very large. When the magnetic field in a ferrous material leaks out and jumps over a flaw or discontinuity in the material, the fields perpendicular to the specimen are very large near the flaw and drop off rapidly away from the flaw. Thus, in ferrous materials, the flaw geometry controlling the sharpness of the image produced.

In nonferrous materials (e.g. aluminum) where the magnetic permeability is low, magnetic fields behave differently near flaws. In order to produce a sharp image of the flaw, it is necessary to produce a field which jumps over the flaw and stays near the flaw.

In order to maximize the imaging potential in nonferrous materials, an electric current at a high frequency (e.g. 30 KHz) is injected into the nonferrous target material. Such current injection results in a magnetic field having appreciable intensity only within skin depth of the flaw as measured parallel to the surface away from the flaw. This concentrated magnetic field area defines the flaw. That is, an image of the magnetic fields on the surface resemble closely the flaw itself in nonferrous materials. Although in the preferred embodiment of the present invention, currents at eddy current frequencies in the range of 10 KHz to 15 MHz or 50 KHz are typically utilized, any suitable current frequency which causes the magnetic field perpendicular to 25 to be small within a skin depth from 28 as measured along the surface of 25 will suffice. In order to obtain useful (persistent) images in this method, a static bias magnetic field (provided by a direct current in coil 24) or other means such as as permanent magnet, must be provided. This bias field, when added to the fields produced by the high frequency eddy currents (at frequency of 10 KHz to 50 KHz) associated with a flow (28) results in an image of the flaw that does not "wash out", but persists even though fields associated with the eddy currents are constantly reversing (at 10 KHz to 50 KHz).

Another method of maximizing the quality of the image produce by the present invention is to utilize a modulated light source. The light source, such as electro-luminescent panel 85 shown in FIG. 6, or the external light source shown in FIG. 2(a), is modulated in brightness in a sinusoidal or other similarly periodic fashion. The predominant frequency of oscillation of the light intensity is the same as that of the current in the coil 24 surrounding the stack. However, the phase of the light source intensity relative to the coil current phase is adjustable. The result is that one can have the light on maximum intensity when the best image (as partially determined by the level of coil current) is present. In this way, the light is only on when a good image can be produced and not on when poor (low contrast) images would be produced. This not only saves energy (the light is on only when the image is good), but does not allow poor images to be averaged in witn good ones which would "wash out" the image. Thus, the frequency of the light modulation (and the coil frequency) can be well above that which the eye can detect. This means not only that the image quality (contrast) will be maximized when the light is on, but will not appear to flicker to the observer. Because the frequency of light modulation can be above that which the eye can detect, the light will appear to the eye to be on all the time, in spite of the fact that the light source intensity is actually being modulated. In practice, a means for adjusting the phase of the light source modulation relative to the current in the coil is provided. The phase is then adjusted until the maximum sharpness or brightness and contrast of the image is produced.

Accordingly, a method and apparatus for the direct visualization of surface and near surface cracks, flaws, etc. in materials has been disclosed. The invention provides a simple and economical means for detecting flaws not possible in the prior art. It will be understood that various changes may be made in the details arrangements and proportions of the various elements of the present invention without departing from the spirit and scope of the invention. For example, it will be apparent that the present invention has utility beyond the detection of flaws in non-organic materials and may be used to detect tumors or other discontinuities in biologic materials.

I claim:

1. An apparatus for detecting flaws, voids, discontinuities, or the like in a target material, comprising:
    a magnetic material having a plurality of magnetic domains, said magnetic material comprising a first magnetic epitaxial layer disposed on a first surface of a non-magnetic substrate;
    a first polarizing layer disposed on a second surface of said non-magnetic substrate oppositely disposed from said first surface of said non-magnetic substrate;
    light generating means disposed between said polarizing layer and said target material, said light generation means being placed in proximity to said target material;
    magnetic field generation means disposed about said magnetic material for generating and applying a variable magnetic field to said target material and to said magnetic material;
    said light generation means projecting light through said polarizing layer and through said magnetic material;
    a second polarizing layer disposed on said first epitaxial layer, said second polarizing layer rotating the plate of polarization of said projected light;
    said polarization plate being rotated dependent on realignment of said magnetic domains caused by magnetic field perturbations in areas of said magnetic material in proximity to a flaw, void, discontinuity or the like, in sid target materials;
    wherein an image of said flaw, void, discontinuity or the like is detected by observing the rotation of said light resulting from magnetic field perturbations in said magnetic material.

2. The apparatus as defined by claim 1, wherein said magnetic field perturbations alter the distribution of said magnetic domains in said magnetic material.

3. The apparatus as defined by claim 2, further including a second epitaxial layer disposed between said substrate and said second polarizing layer.

4. The apparatus as defined by claim 3, further including a reflective coating disposed on first and second epitaxial layers.

5. The apparatus as defined by claim 4, wherein the rotation of the plane of polarization of the incident light on said magnetic epitaxial layer is described by the following relationship:

$$\theta \propto \theta_f \overline{K} \cdot \overline{M}$$

where,
$\theta_f$ = the specific Faraday rotation of said magnetic epitaxial layer,
$\overline{K}$ = the wave vector of the incident polarized light,
$\overline{M}$ = the local magnetization of said magnetic epitaxial layers.

6. The apparatus as defined by claim 5, wherein said magnetic field perturbations constitute field reversals in proximity to a boundary of a flaw, void or the like in said target material.

7. The apparatus of claim 1, wherein current is injected into said target material at a frequency sufficient to produce magnetic field variations at the surface of said target material corresponding to flaws contained within said target material.

8. An apparatus for detecting and providing images of flaws, voids, discontinuities, or the like in a target material under ambient light conditions, comprising:
    a magnetic material having a plurality of magnetic domains, said magnetic material comprising a first magnetic epitaxial layer disposed on a first surface of a non-magnetic substrate:
    a first partially reflecting layer disposed on a second surface of said substrate oppositely disposed from said first surface of said non-magnetic substrate;
    a second partially reflecting layer disposed on said first epitaxial layer, said first and second partially reflective layers for reflecting ambient light;
    a polarizing layer disposed on said first partially reflecting layer;
    light generation means disposed between said first polarizing layer and said target material, said light generation means being placed in proximity to said target material;
    a second polarizing layer disposed on said second partially reflecting layer;
    magnetic field generation means disposed about said magnetic material for generating and applying a variable magnetic field to said target material and said magnetic material;
    said light generation means projecting light through said first polarizing layer, through said first partially reflecting layer, through said magnetic material, through said second partially reflecting layer and through said second polarizing layer;
    said magnetic material rotating the plane of polarization of said reflected light as a result of the realignment of said magnetic domains caused by magnetic field perturbations, in areas of said magnetic material in proximity to a flaw, void, discontinuity, or the like, in said target material;
whereby the image of said flaw, void, discontinuity, or the like is detected by observing the rotation of said light resulting from magnetic field perturbations in said magnetic material.

9. The apparatus of claim 8, wherein said magnetic field perturbations alter the distribution of said magnetic domains in said magnetic material.

10. The apparatus of claim 9, further including a second epitaxial layer disposed between said substrate and said second partially reflecting layer.

11. The apparatus of claim 10, further including a reflective coating disposed on said first and second epitaxial layers.

12. The apparatus as defined by claim 8, wherein the rotation of the plane of polarization of the incident light on said magnetic epitaxial layer is described by the following relationship:

$$\theta \propto \theta_f \overline{K} \cdot \overline{M}$$

where,
$\theta_f$ = the specific Faraday rotation of said magnetic epitaxial layer,
$\overline{K}$ = the wave vector of the incident polarized light,
$\overline{M}$ = the local magnetization of said magnetic epitaxial layer.

13. The apparatus as defined by claim 8, wherein said magnetic field generation means generates an alternating (AC) magnetic field, and said incident polarized light is modulated in synchrony with said magnetic field such that the output of said analyzer remains substantially constant.

14. The apparatus as defined by claim 13, wherein a current is injected into said target material at a frequency sufficient to generate a rotation in the plane of the magnetic field at the surface of said target material corresponding to any flaws located within said target material.

* * * * *